United States Patent [19]

Weber et al.

[11] Patent Number: 4,952,734
[45] Date of Patent: Aug. 28, 1990

[54] PROCESS FOR THE PREPARATION OF METHYLAMINES

[75] Inventors: Jürgen Weber, Oberhausen; Detlef Kampmann, Bochum; Claus Kniep, Oberhausen, all of Fed. Rep. of Germany

[73] Assignee: Hoechst AG Werk Ruhrchemie, Fed. Rep. of Germany

[21] Appl. No.: 210,633

[22] Filed: Jun. 23, 1988

[30] Foreign Application Priority Data

Jun. 30, 1987 [DE] Fed. Rep. of Germany ....... 3721539

[51] Int. Cl.$^5$ .............................................. C07C 85/02
[52] U.S. Cl. .................................... 564/471; 564/472; 564/473; 564/474
[58] Field of Search ................ 564/471, 472, 473, 474

[56] References Cited

U.S. PATENT DOCUMENTS 3,136,819  6/1964  Shapiro et al. ...................... 564/471
4,621,158  11/1986  Hubert et al. ...................... 564/471

FOREIGN PATENT DOCUMENTS 0142868  5/1985  European Pat. Off. .
1932422  9/1971  Fed. Rep. of Germany .
3544510  6/1987  Fed. Rep. of Germany .

Primary Examiner—Richard L. Raymond
Assistant Examiner—Raymond Covington
Attorney, Agent, or Firm—Bierman and Muserlian

[57] ABSTRACT

A process for the preparation of methylamines by the reaction of amines, formaldehyde and hydrogen as starting materials on a fixed-bed catalyst in the liquid phase under pressure and preferably at elevated temperature. The starting materials contain a reduced percentage of water. They are heated to a predetermined temperature apart from each other, and then mixed with each other in the presence of the fixed-bed catalyst.

19 Claims, No Drawings

PROCESS FOR THE PREPARATION OF METHYLAMINES

This Application claims the priority of German Application P 37 21 539.6, filed Jun. 30, 1987.

The present invention relates to a process for the preparation of methylamines by the reaction of starting amines with formaldehyde and hydrogen on a fixed-bed catalyst in liquid phase. Monovalent or multivalent primary or secondary amines, as well as mixtures thereof, can be used as starting amines. The reaction usually takes place at elevated temperature and generally requires elevated pressure. Depending on the selected reaction conditions, it leads to partial or complete replacement of the hydrogen atoms on the amine nitrogen atom by methyl groups, water being formed. This reaction is, therefore, also called hyrogenating N-methylation of amines.

Tertiary amines are important compounds commercially. They can serve as polymerization and curing catalyst for the manufacture of plastics based on epoxy and urethane. Furthermore, they are suitable as corrosion inhibitors and adsorption agents for synthesis gas washing. This applies in particular to the easy-to-produce methyl and dimethyl derivatives.

The hydrogenating methylation of amines with formaldehyde and hydrogen is an important synthesis method for the preparation of such methylated amines. A summary of this process is to be found in Houben-Weyl, Methoden der organischen Chemie; Volume XI/1, 4th edition (1957), pages 641 to 647.

Generally, it is not possible to convert discontinuous (batch) processes to a continuous reaction of amines with formaldehyde and hydrogen. There are various reasons for this. Pressure-resistance tubular reactors containing the hydrogenation catalyst in lump form are used in continuous N-methylation. The starting materials, or their reaction mixtures, are fed into the tubular reactor either at the head or the bottom. Depending on the type of feed, one speaks of a trickling or a bottom-feed operation. When used over a prolonged period, the hydrogenation catalyst decompose to an increasing degree. The resultant fine particles cause fouling, either in the tubular reactors or in the downstream plant sections. This leads to an increase in pressure in the reaction apparatus which automatically means that the reaction has to be stopped to clear the blockage.

The incidence of formic acid, which probably forms from formaldehyde through the Cannizzaro reaction, is also undesirable. It withdraws a corresponding amount of amine from the reaction in the form of a salt. The free acid and the amine salt both promote corrsion in the reactor system.

Other side reaction impairing continuous reaction are the result of the polymerization of formaldehyde and the polycondensation between the amine and formaldehyde to hexahydrotriazines or, in the case of multivalent amines, to higher molecular weight compounds. The formation of polymeric substances leads to the catalyst charge becoming sticky and, therefore, to blockage of the reactor. The unavoidable result is the necessity for changing the catalyst. These well-known disadvantages can be avoided in various ways.

In order to avoid premature decomposition of the catalyst DE-A 25 45 695 recommends the use of a pretreated cobalt or nickel catalyst. The pretreatment consists in using catalyst for a standard hydrogenation or amination process before employing it for hydrogenation N-methylation.

DE-A 26 18 580 teaches the use of a special, unsupported catalyst containing at least 60% cobalt, 10 to 30% copper. The reaction mixtures is passed, in a liquid phase, through the hydrogenation reactor, during which passage a reaction temperature of 110° C. should not be exceeded. The starting amine and formaldehyde are added to the liquid phase outside the reactor in order to avoid side reactions.

EP-A 0 142 868 recommends the use of hydrogenation catalyst on activated carbon for the N-methylation of amines. Supported catalyst on the basis of aluminum oxide, silicon oxide and silica are undesirable owing to poor distribution of the catalyst. Support-free metal catalysts are highly active but do not produce good results.

As can be seen from the afore-mentioned state of the art, there is no shortage of attempts to avoid the difficulties encountered in the reaction of amines with formaldehyde and hydrogen through the use of special catalysts. Therefore, there is a demand for a process which is both easy to perform and permits the use of standard hydrogenation catalysts for N-methylation. It should not only produce high yields with high selectivity, but also be generally applicable, i.e. independent of the type of amine.

These requirements are met by a process for the preparation of methyl amines by the reaction of amines, formaldehyde and hydrogen as starting materials under pressure and at a reaction temperature on a fixed-bed catalyst in the liquid phase. It is characterized in that the starting materials, in particular the formaldehyde, contain a reduced percentage of water, they are heated to a predetermined temperature apart from each other, and then mixed with each other in the presence of the fixed-bed catalyst.

The starting materials are reacted at 0.1 to 30, preferably 1 to 20, and most preferably 2 to 15 MPa. The reaction temperature is 20° to 250° C., preferably 50° to 200°, and most preferably 70° to 150° C. The process according to the invention can be operated discontinuously or continuously; it is particularly suitable for continuous operation.

Standard hydrogenation catalysts can be used as the fixed-bed catalyst. The pressure and temperature are, to a certain degree, dependent on the type of catalyst and they must be adapted thereto, as is known to the person of ordinary skill in the art.

The reaction can take place in a straight run and with the aid of a reaction product cycle. The starting materials can be fed into the reactor in which the catalyst is located at the head or at the bottom. According to a particular embodiment of the invention, the feed materials are passed into the reactor at the bottom and the reaction takes place in a straight run; i.e. without the reaction product being recycled. The reaction mixture leaves the reactor at the head.

The process according to the invention is independent of the type of amines used. It can generally be used with all organic compounds with one or several primary or secondary amine groups. Monovalent and/or multivalent primary and/or secondary amines can also be employed. Aliphatic or cycloaliphatic amines can be used in the N-methylation according to the invention, as well as araliphatic, aromatic, or heterocyclic amines. Mixtures of said amines are also useful.

The amines preferably have a total of 1 to 40 carbon atoms. The substituents available can be straight-chain and/or branched alkyl groups with 1 to 20 carbon atoms, substituted and/or unsubstituted cycloalkyl groups with 5 to 20 carbon atoms, substituted and/or unsubstituted aromatic groups with 6 to 20 carbon atoms, or heterocyclic groups with 4 to 20 carbon atoms which can contain oxygen, sulfur and/or nitrogen as a heteroatom. The amines can have the same or different substituents of the aforementioned type.

Examples of aliphatic amines are: methylamine, ethylamine, propylamine, n- and i-butylamine, pentylamine, hexylamine, 2-ethylhexylamine, octylamine, dodecylamine, stearylamine, dimethylamine, diethylamine, dipropylamine, dibutylamine, dipentylamine, dihexylamine, di-2-ethylhexylamine, dioctylamine, ethylenediamine, 1,3-diaminopropane, 1,4-diaminobutane, 1,6-diaminohexane (hexamethylenediamine-(1,6)), polyalkylenepolyamine, hexamethylenetetramine, ethanolamine, propanolamine and diethanolamine.

Examples of cycloaliphatic amines are: cyclopentylamine, cyclohexylamine and tricyclodecanamines. The ring systems can carry substituents, in particular, alkyl groups. Examples of araliphatic amines are: benzylamine, alpha and beta-phenylethylamine, N-methylbenzylamine, and dibenzylamine.

Examples of aromatic amines are: aniline, toluidine, N-alkylated anilines and toluidines, benzidine (4.4'-diaminodiphenyl), phenylene diamine, diphenylamine, and substituted and unsubstituted naphthylamines. Examples of heterocyclic amines are: piperidine, piperazine, pyrrole, and diazoles.

An important factor for the success of the process according to the invention is that the mixture present in the reactor has a reduced percentage of water. Too high a percentage of water is undesirable as it damages the fixed-bed catalyst. On the one hand, it impairs the activity of the catalyst and reduces both conversion and selectivity of the reaction; on the other hand, it leads to a rapid decomposition of the fixed-bed catalyst.

The water content is limited by using starting materials with reduced water content. Generally, the amine exhibits only minor amount or traces of water. On the other hand, there are considerable amounts of water in standard commercial formaldehyde which can contain approximately 60% water by weight and more. In addition to the water which is brought into the reaction with the starting materials, there is also the reaction water which is generated during the reaction. The total amount of water, based on the liquid-gas mixture flowing around the fixed-bed catalyst, should not exceed 50% by weight.

It is particularly expedient to limit the water content of the formaldehyde solution. It should not exceed a value of 50% by weight based in the formaldehyde solution. Formaldehyde solutions with 0 to 50% water by weight are suitable. Those with 5 to 30% by weight have proved to be more suitable. Formaldehyde with 7 to 15% by weight is most preferred. Paraformaldehyde can also be successfully used, e.g. in suspended form.

Regardless of the amount of water introduced into the reaction with the starting materials, the water content in the reaction mixture increases due to the formation of reaction water. This increase in the percentage of water can lead to the formation of a heterogeneous, liquid product mixture consisting of organic and aqueous parts. The resultant aqueous phase settles to the bottom of the reactor and prevents reaction in those areas where it covers the fixed-bed catalyst.

In order to avoid the formation of an undesirable aqueous phase, the addition of a solvent capable of dissolving both water and organic compounds is necessary. Suitable solvents are, for example, aliphatiic alcohols with 1 to 5 carbon atoms, ethers such as tetrahydrofurane and dioxane, as well as dimethylsulfoxide and mixtures of the above-mentioned substances. The solvent can be added both to the amine and to the formaldehyde.

Another important factor in the process according to the invention is that the starting materials are heated to a predetermined temperature apart from each other. This means that the amine, formaldehyde and hydrogen are passed through their own pipes and heated before the reaction is performed.

The hydrogen can also be introduced into the reaction mixed with either the amine or the formaldehyde and then preheated. It is also possible to spread the hydrogen over the amine and the formaldehyde. According to a preferred embodiment of the invention, the hydrogen is mixed with amine and heated. On the other hand, it is not permissible to mix the amine and formaldehyde and heat them before the reaction takes place. The amine and formaldehyde must always be kept separate from each other and heated to the predetermined temperature.

The predetermined temperature depends primarily on the reaction temperature. It should not be more than 20°, in particular 10°, and preferably 5° C. below the reaction temperature and not more than 10°, preferably 5°, and most preferably 0° C. above the reaction temperature.

After the starting materials have been heated to the predetermined temperature, they are mixed together in the presence of the fixed-bed catalyst. The starting amine and formaldehyde may only come into contact with each other in the presence of the fixed-bed catalyst.

If the hydrogen is added to the reaction together with one of the other starting materials, the amine and the formaldehyde may only be added in the presence of the fixed-bed catalyst. In this case as well, all three starting materials only come into contact with each other in the pesence of the catalyst. In engineering terms, this requirement is met by terminating the pipe or the pipe system of at least one of the starting amine and formaldehyde in the catalyst zone. This insures that the amine comes into contact with the formaldehyde in the presence of the catalyst.

According to a perferred embodiment of the invention, the formaldehyde is introduced through a pipe terminating in the catalyst zone.

However, it is also possible to have the pipes of two or even all three starting materials terminating in the zone of the fixed-bed catalyst. The arrangement of the pipes to be chosen will depend both on the amounts of starting materials, and on the geometry of the catalyst zone and the required flow ratios. If the throughputs of the substances are to be substantial per time unit, it is desirable to use several pipes per starting material. Should the flow ratios not ensure sufficient mixing of the reactants in the catalyst zone, the use of addtional disribution devices is useful. These distributors can, for example, be mounted as ring showers or shower heads at the end of the pipe. However, other distributor systems such as nozzles, frits, or pipe bundles can also be used.

The process according to the invention has one decisive advantage over the state of the art. It is not restricted to the use of special catalysts but permits the use of a large number of conventional fixed-bed catalyst. The well-known disadvantages—damage to the catalyst and the formation of undesirable by-products—are avoided. Decomposition of the catalyst is effectively prevented, as is the formation of polymer products.

The fixed-bed catalysts can be supported butt also support-free. They contain Ni, Co, Cu, Mn, Fe, Rh, Pd and/or Pt, preferably Ni, Co, Cu, Rh, Pd and/or Pt and, most preferably, Ni, Co and/or Pd. If desired, standard additives and promoters, for example alkaline earth oxides, $SiO_2$, $Al_2O_3$, $MnO_2$ and/or $Cr_2O_3$, may be included.

The use of supported catalysts is advantageous. $Al_2O_3$, $SiO_2$, activated carbon, and pumice stone can be used advantageously as supports. It is particularly favorable to use catalysts with 10 to 75, in particular 20 to 70, preferably 40 to 65% by weight Ni, Co, Cu, Mn and/or Fe based on the total catalyst mass.

Noble metal catalysts permit reaction under particularly mild conditions. They are customarily applied to a support and have a metal content of 0.1 to 20, preferably 0.2 to 15, and most preferably 0.5 to 10% by weight based on the total catalyst mass.

Suitable noble metals are Rh, Pd and/or Pt. Formed materials based on $Al_2O_3$, $SiO_2$, activated carbon, silica gel, kieselguhr, and/or pumice stone are recommended as supports. The catalyst determines the reaction conditions, in particular the reaction temperature and pressure.

Noble metal catalysts require temperatures of 20° to 165°, preferably 30° to 160°, and most preferably 50° to 150° C. and pressures of 0.1 to 15, preferably 0.2 to 12, and most preferably 0.5 to 10 MPa. Particularly mild conditions are provided by temperatures up to 100° C. A more rapid reaction takes place at temperatures ranging from 100° to 165°, especially 110° to 160°, and most preferably 115° to 150° C.

The Ni, Co, Cu, Mn and/or Fe-containing base metal catalysts require temperatures of 50° to 250°, preferably 70° to 200°, and most preferably 100° to 150° C. and pressures of 3 to 30, preferably 5 to 20, and most preferably 8 to 15 MPa.

The ratio of the hydrogen atoms on the amine nitrogen to be replaced by methyl groups to the formaldehyde is 1:1 to 1:2, preferably 1:1 to 1:1.5, and most preferably, 1:1 to 1:1.2. 1 to 10, in particular 1.05 to 5, and preferably 1.1 to 2.5 moles of $H_2$ are added to the reaction per mol of formaldehyde. The hydrogen employed in excess can be recycled.

The catalyst load (volume feed mixture/bulk density of the catalyst×hour=V'/Vh) is 3:1 to 0.2:1, preferably 2:1 to 0.4:1, and most preferably 1.5:1 to 0.5:1.

EXPERIMENTAL SECTION

The reactor vessel consists of a pressure-resistance pipe with an inside diameter of 28 mm. Raschig rings with a diameter of 3 mm are charged into the bottom of the pressure pipe to a height of 800 mm. This zone serves as the preheating zone in which the starting materials are heated by a heating jacket to the predetermined temperature. The fixed/bed catalyst is located above the pre-heating zone.

The reactor is filled with amine at the beginning of the reaction. The starting materials are pumped into the bottom of the reactor, the reaction mixture is drawn off above the catalyst zone and passed to a pressure separator.

More amine is fed into the reactor together with hydrogen and flows through the pre-heating zone filled with Raschig rings. The formaldehyde is pumped directly into the fixed-bed catalyst layer via a separate ascension piep which passes through the pre-heating zone and is only mixed with the amine and hydrogen at the layer. The preheating zone and the starting materials are heated by means of the heating jacket surrounding the outside of the reactor to the desired predetermined temperature. After leaving the catalyst zone, the reaction mixture is withdrawn from the head of the reactor and fed into a pressure separator.

EXAMPLE 1

Continuous preparation of N,N-dimethyl-n-octylamine 300 ml of a Ni-catalyst in tablet form (50 to 53% Ni by weight and a product of Hoechst AG: type RCH Ni 52/35 and about 25 to 30% kieselguhr by weight as support; are charged into the reactor vessel described above. The reactor is filled with n-octylamine. Then 60 ml n-octylamine/hour (V'/Vh=0.2) or 120 ml n-octylamine/hour (V'/Vh=0.4) and excess hydrogen (200 liters $H_2$/hour) are added at 120° C. and 10 MPa $H_2$ pressure. Formaldehyde (55% formaldehyde, 35% methanol and 10% water, all by weight) is added in an excess of 10 mol % based on the amine.

The reaction mixture thus formed is withdrawn from the head of the reactor vessel and separated from the excess hydrogen in a downstream pressure separator. The results obtained are listed in Table 1. The figures determined by gas chromatography relate to water-free product.

TABLE 1

| Product composition | V'/Vh = 0.2* | V'/Vh = 0.4* |
|---|---|---|
| Methanol | 28.4 | 28.5 |
| N-methyl-n-octylamine | 2.5 | 3.6 |
| N,N-dimethyl-n-octylamine | 68.9 | 66.7 |
| Higher boiling products | 0.2 | 1.2 |

*based on n-octylamine feed

EXAMPLE 2

Continuous preparation of N,N-dimethylaniline

The same procedure and apparatus as in Example 1 are used, except as follows. The reactor is filled with aniline. Then 90 ml anline/hour (V'/Vh+0.3) and excess hydrogen (200 liters $H_2$/hour) are fed in at 110° C. and 10 MPa $H_2$ pressure. Formaldehyde is added as described in Example 1. The reaction mixture separates into two phases. The upper phase contains nearly all the water and the majority of the methanol. The lower layer consists of desired end product.

The results obtained (wt. % based on water-free product) are to be seen in Table 2 below.

TABLE 2

| Product composition (lower phase) | |
|---|---|
| methanol | 7.5% |
| intermediate runnings | 5.5% |
| aniline | 1.2% |
| N,N-dimethylaniline | 75.8% |
| higher boilers | 10.0% |

TABLE 2-continued

| Product composition (lower phase) | |
|---|---|
| water content | 0.7% |

EXAMPLE 3

Continuous manufacture of N,N-dimethylpiperazine

The same procedure and apparatus as in Example 1 are employed except as follows. The reactor is filled with piperazine. Then 215 ml piperazine solution/hour (volume ratio piperazine:$CH_3OH$=1:1) and excess hydrogen (200 liters $H_2$/hour) are fed in at 110° C. and 10 MPa $H_2$ pressure. Formaldehyde is added as described in Example 1.

The results obtained (wt. % based on water-free product) are to be seen in Table 3 below.

TABLE 3

| Product composition | |
|---|---|
| methanol | 37.1% |
| intermediate runnings | 0.1% |
| N,N'-dimethyl-piperazine | 62.2% |
| N-methyl-piperazine | 0.1% |
| piperazine | 0.3% |
| higher boilers | 0.2% |

N,N'-dimethyl piperazine is obtained in 99% purity by this method.

EXAMPLE 4

Continuous manufacture of N,N-dimethyldiglycolamine

The same procedure and apparatus as in Example 1 are employed except as follows. The reactor is filled with diglycolamine. Then 100 ml diglycolamine/hour (V'/Vh=0.33) or 150 ml diglycolamine/hour (V'/Vh=0.5) are fed in at 120° C. and 10 MPa $H_2$ pressure. Formaldehyde is added as described in Example 1.

The results obtained (wt. % based on to water-free product) are to be seen in Table 4 below.

TABLE 4

| V'/Vh | 0.33 | 0.5 | 0.5 |
|---|---|---|---|
| Product composition | | | |
| first runnings | <0.1 | 0.1 | 0.1 |
| methanol | 29.9 | 29.2 | 28.5 |
| intermediate runnings | 0.4 | 0.3 | 0.4 |
| N,N'-dimethyldiglycolamine | 49.8 | 49.8 | 49.8 |
| final runnings | 0.2 | 0.3 | 0.4 |
| $H_2O$ | 19.7 | 20.3 | 20.8 |

EXAMPLES 5 to 12

Continuous manufacture of N,N-dimethyl-n-octylamine

The same procedure and apparatus as in Example 1 is employed except as follows.

300 ml each of a palladium catalyst (5 wt. % Pd on an aluminum oxide support in tablet form; proprietary product of Degussa: type E 263P); a cobalt catalyst (43 to 46% Co by weight, kieselguhr as a support; proprietary product of Hoechst AG: type RCH Co 45/20); a copper catalyst (approx. 60% Cu, by weight, $SiO_2$ as support; priorietary product of Hoechst AG: type RCH Cu 60/35); and a platinum catalyst (5 wt. % Pt on granular activated carbon) are used as catalysts.

The reactor is filled with n-octylamine. Then 90 ml or 75 ml n-octylamine/hour (V'/Vh=0.3 or 0.25) and excess hydrogen (200 liters $H_2$ hour) are fed in at 120° C. and 5 or 10 MPa $H_2$ pressure. Formaldehyde is added as described in Example 1. The reaction conditions and product composition (wt. % related to anhydrous product) are to be seen in Table 5.

TABLE 5

| Example | 5 | 6 | 7 | 8 | 9 | 10 | 11 | 12 |
|---|---|---|---|---|---|---|---|---|
| Catalyst | Degussa E263P | | RCH Co 45/20 | | RCH Cu 60/35 | | Pt on granulated activated carbon | |
| Reaction temperature (°C.) | 120 | | 120 | | 120 | | 120 | |
| Pressure (MPa $H_2$) | 10 | 5 | 10 | 5 | 10 | 5 | 5 | 10 |
| V'/Vh | 0.30 | | 0.25 | | 0.25 | | 0.25 | 0.25 |
| Product composition | | | | | | | | |
| Methanol | 21.8 | 20.9 | 33.7 | 37.6 | 31.3 | 23.1 | 19.1 | 21.7 |
| intermediate runnings | 2.3 | 1.5 | 2.1 | 1.2 | 1.7 | 1.7 | 3.7 | 3.4 |
| N,N-Dimethyl-n-octylamine | 75.7 | 77.6 | 59.6 | 56.0 | 66.4 | 74.2 | 76.8 | 73.9 |
| Intermediate runnings | — | — | — | — | 0.4 | 1.0 | 0.4 | 0.5 |
| N,N-Dioctyl-methylamine | 0.2 | — | 4.4 | 5.2 | — | — | — | 0.5 |
| Higher boilers | — | — | 0.2 | — | 0.2 | — | — | — |

What we claim is:

1. A process for the preparation of methylamines by the liquid phase reaction of the starting amine, formaldehyde and hydrogen under pressure and at a reaction temperature on a fixed-bed catalyst, the improvement comprising separately heating the formaldehyde containing a reduced percentage of water and the amine to a preset temperature and then mixing the reactants together in the presence of the fixed-bed catalyst while maintaining the amount of water present in the reaction mixture not more than 50% by weight.

2. The process of claim 1 wherein said solution contains 5 to 30% water by weight.

3. The process of claim 2 wherein said solution contains 7 to 15 % water by weight.

4. The process of claim 1 wherein the pressure is 0.1 to 30 and said reaction temperature is 20° to 250° C.

5. The process of claim 1 wherein said pressure is 1 to 20 MPa and said temperature is 50° to 200° C.

6. The process of claim 2 wherein said pressure is 2 to 15 MPa and said temperatue is 70° C. to 150° C.

7. The process of claim 1 wherein said starting amine is taken from the class consisting of organic compounds having at least one primary and/or secondary amine group and mixtures thereof.

8. The process of claim 1 wherein said starting amine is monovalent and/or multivalent.

9. The process of claim 1 wherein said starting amine is aliphatic, cycloaliphatic, araliphatic, aromatic, and/or heterocyclic.

10. The process of claim 1 wherein said predetermined temperature is from 20° C. below said reaction temperature to 10° C. above said reaction temperature.

11. The process of claim 10 wherein said predetermined temperature is from 10° C. below said reaction temperature to 5° C. above said reaction temperature.

12. The process of claim 11 wherein predetermined temperature is from 5° C. below said reaction temperature to 0° C. above said reaction temperature.

13. The process of claim 1 wherein said predetermined temperature is 20° to 0° C. below said reaction temperature.

14. The process of claim 13 wherein said predetermined temperature is 10° to 0° below said reaction temperature.

15. The process of claim 14 wherein said predetermined temperature is 5° to 0° below said reaction temperature.

16. The process of claim 1 wherein said catalyst is a metal catalyst.

17. The process of claim 16 wherein said catalyst contains Ni, Co, Cu, Mn, Fe, RH, Pd and/or Pt.

18. The process of claim 16 wherein said catalyst contains $Al_2O_3$, $SiO_2$, or activated carbon as a support.

19. The process of claim 16 wherein there is present at least one substance taken from the class consisting of alkaline earth metal oxides, $SiO_2$, $Al_2O_3$, $MnO_2$, and $Cr_2O_3$.

* * * * *